(12) United States Patent
Barnes, Sr. et al.

(10) Patent No.: US 7,938,776 B2
(45) Date of Patent: May 10, 2011

(54) EXAMINATION DEVICE FOR BLOOD DETECTION

(75) Inventors: Albert T. Barnes, Sr., Pottsville, PA (US); Albert T. Barnes, Jr., Minersville, PA (US)

(73) Assignee: Mederistic Solutions, Inc., Pottsville, PA (US)

(*) Notice: Subject to any disclaimer, the term of this patent is extended or adjusted under 35 U.S.C. 154(b) by 0 days.

(21) Appl. No.: 12/050,306

(22) Filed: Mar. 18, 2008

(65) Prior Publication Data

US 2009/0240130 A1 Sep. 24, 2009

(51) Int. Cl.
*A61B 5/00* (2006.01)

(52) U.S. Cl. .............................. 600/371; 422/56; 436/66

(58) Field of Classification Search .................... 422/56; 436/66; 600/572
See application file for complete search history.

(56) References Cited

U.S. PATENT DOCUMENTS

| | | |
|---|---|---|
| 2,084,692 A | 6/1937 | Little |
| 2,394,140 A | 2/1946 | Biscow |
| 2,847,012 A | 8/1958 | Eastman |
| 3,012,976 A | 12/1961 | Adams et al. |
| 3,362,408 A | 1/1968 | Stocki et al. |
| 3,672,351 A | 6/1972 | Ubersax et al. |
| 3,867,947 A | 2/1975 | Schack |
| 3,996,006 A | 12/1976 | Pagano |
| 4,005,984 A | 2/1977 | Alsop |
| 4,092,120 A | 5/1978 | Suovaniemi et al. |
| 4,245,656 A | 1/1981 | Farr et al. |
| 4,327,744 A | 5/1982 | Smith |
| 4,357,945 A | 11/1982 | Janko |
| 4,420,353 A | 12/1983 | Levine |
| 4,473,079 A * | 9/1984 | Jasper et al. ................. 600/371 |
| 4,559,949 A | 12/1985 | Levine |
| 4,578,358 A | 3/1986 | Oksman et al. |
| D284,215 S | 6/1986 | Sherwin et al. |
| 4,645,743 A | 2/1987 | Baker et al. |
| 4,804,518 A | 2/1989 | Levine et al. |
| 4,808,379 A | 2/1989 | Wardlaw et al. |
| 4,843,014 A | 6/1989 | Cukier |
| 4,876,067 A | 10/1989 | Deneke et al. |
| 4,910,803 A | 3/1990 | Cukier |
| 4,937,197 A * | 6/1990 | Lawrence ....................... 436/66 |
| 5,064,766 A | 11/1991 | Wardlaw et al. |
| 5,182,191 A | 1/1993 | Fan et al. |
| 5,423,090 A | 6/1995 | Gimbel |
| 5,840,584 A | 11/1998 | Waldenburg |
| 5,867,831 A | 2/1999 | Husain |
| 5,976,881 A | 11/1999 | Klingner |
| 6,027,511 A | 2/2000 | Shirley et al. |

(Continued)

OTHER PUBLICATIONS

U.S. Appl. No. 10/653,806, filed Sep. 2, 2003, now abandoned.

*Primary Examiner* — Charles A Marmor, II
*Assistant Examiner* — Michael D'Angelo
(74) *Attorney, Agent, or Firm* — Keith R. Lange

(57) ABSTRACT

The present invention describes examination devices, such as examination gloves, for detecting the presence of blood, and in particular hidden blood, in biological samples. Examination devices according to the present invention include, in certain embodiments, developer and indicator reagents in a single encapsulation, which offers numerous clinical and other benefits. Kits including devices according to the present invention in sterile packaging, and methods of making and using devices according to the present invention, are also described.

14 Claims, 7 Drawing Sheets

U.S. PATENT DOCUMENTS

| | | |
|---|---|---|
| 6,370,694 B1 | 4/2002 | Michelson |
| 6,409,734 B1 | 6/2002 | Zapata |
| 6,896,681 B1 | 5/2005 | Watson |
| 6,939,311 B2 | 9/2005 | Geiger |
| 2001/0056227 A1* | 12/2001 | Gopinathan et al. ......... 600/300 |
| 2003/0120180 A1* | 6/2003 | Kaylor et al. ................ 600/584 |
| 2004/0176706 A1* | 9/2004 | Geiger ......................... 600/584 |

* cited by examiner

EXAMINATION DEVICE FOR BLOOD DETECTION

FIELD OF THE INVENTION

The present invention relates to examination devices, including examination gloves, for determining the presence of blood in biological samples. In particular, the present invention relates to examination devices, such as examination gloves, for readily detecting the presence of blood in stool samples during a medical procedure such as a colorectal examination.

BACKGROUND OF RELATED TECHNOLOGY

The presence of blood in biological samples may be indicative of a serious medical problem, such as an internal injury or disease. As such, various testing procedures have been developed to test for the presence of blood, and in particular to test for hidden (occult) blood in biological samples. For example, blood that is present in a patient's stool may be the result of injury or disease at any point along the digestive tract, and may be indicative of anything from a minor perforation in the digestive tract lining to serious colorectal disease such as colon cancer. Early detection of occult blood is critical, as it is often the first, and may be the only, symptom of such injury or disease.

Various noninvasive tests have been developed to detect the presence of occult blood in biological material, such as stool. For example, typical fecal occult blood tests include guaiac smear tests (sold as Hemoccult®, Seracult®, Instaccult®, and Coloscreen®), and flushable reagent pads (sold as EZ DetectT® and ColoCARE®). While generally accurate, both types of tests have various disadvantages.

Diagnostically, guaiac smear tests are favored for colon cancer screening due to their established clinical use, because the results are generally interpreted by a medical professional (who is trained to determine false positive and false negative results), and because the medical professional is best able to advise and further test/treat the patient in the event of a positive test result, and ensure patient compliance with needed follow-up care. The use of such tests is well-described in the medical literature (See, for example, Greegor, D. H., (1969) *Cancer* 19; 330-337; Hastings, J. B., (1974) *Amer. J. Surg.* 127:228-233). In general, these tests involve placing a fecal sample on an absorbent paper coated with guaiac and adding a developer reagent containing hydrogen peroxide. If hemoglobin is present, the guaiac is oxidized, turning the paper blue.

In the event of a positive test result, the medical professional may perform a sigmoidoscopy to observe the rectum and lower colon for abnormalities, a colonoscopy to thoroughly observe the rectum and entire colon, and/or a barium enema followed by a series of x-rays to view abnormalities in the colon and rectum. However, the need that such tests generally be performed during medical visits results in relatively infrequent testing, and, as such, an injury or disease may go undetected and consequently untreated for a relatively long period of time. As such, they are not necessarily well-suited for the early detection of colorectal problems.

Further, while such tests may be prescribed to patients for in-home use, this is generally not favored due to the stool handling and procedural requirements needed to ensure that the test is properly performed, which also results in relatively poor patient compliance, and, in the event of a positive test result, requires the patient to visit the doctor in order to obtain further necessary testing and/or treatment, increasing the likelihood that certain patients will not receive such further medical care. Some medical professionals also question whether such tests should be relied on for the screening of colorectal cancer (see in this regard, for example, H. Bleiberg, *Annals of Oncology* (2002) 13:44-46).

Flushable reagent pads, on the other hand, are more suitable for in-home use, as they are generally available without a prescription and do not require direct stool handling or laboratory processing. However, they have certain disadvantages, including that they are not preferred diagnostically because they rely on the dispersal of occult blood in the toilet to ensure a reaction with the developer (and at the threshold sensitivities), and must be viewed in (or removed from) the toilet bowl to determine the test results. Furthermore, they have only been on the market for a relatively short time.

Various attempts have been made to develop alternative examination devices that afford certain of the diagnostic and compliance benefits of the aforementioned tests, but such devices have various disadvantages rendering them clinically and/or otherwise unsuitable. In this regard, for example, U.S. Pat. No. 4,473,079 discloses an examination glove having an indicator impregnated in a filter pad at the base of the thumb, and a solid peroxide compound dispersed in a spreadable material at the tip of the thumb. In use, a stool sample is obtained at the index finger, coverings on each of the dispersed peroxide and indicator compounds are removed by the patient using his alternate hand, the stool sample is contacted with the peroxide compound, and this mixture is then rubbed onto the indicator-impregnated filter paper at the base of the thumb. However, such devices as those described in the aforementioned '079 patent include numerous drawbacks that render them unsuitable for clinical use, including, for example, the need for specialized peroxide preparations, the availability of the chemicals to react with the ambient environment, the need for two-handed operation, and their general unsuitability for use by certain patients (for example, patients suffering from arthritic conditions cannot use such devices as, in use, the fingers must be bent to a significant degree in order to carry out the procedure).

SUMMARY OF THE INVENTION

Generally speaking, the present invention addresses some or all of the above-described problems in the art by providing examination devices, such as examination gloves, for detecting the presence of blood, and in particular hidden blood, in biological samples. Examination devices according to the present invention include, in certain embodiments, developer and indicator reagents in a single encapsulation, which affords numerous clinical and other benefits over known devices. The present invention also provides in certain embodiments for kits including examination devices according to the present invention in sterile packaging and which may be provided with instructions for use, as well as methods of making and using examination devices according to the present invention.

In certain example (non-limiting) embodiments, there is provided by the present invention an examination device for detecting the presence of blood in a sample, including a first finger receiving member having a first open end, a second closed end, and a sample collection area generally located proximal the second closed end thereof for receiving a sample to be tested for the presence of blood, and a second finger receiving member located spaced apart from the first finger receiving member and having a first open end, a second closed end, and at least one reagent capable of reacting with a blood component, wherein, when a sample containing blood is received at the sample collection area of the first finger receiving member and caused to contact the at least one reagent at the second finger receiving member, a visible indication that the sample contains blood results at the second finger receiving member, and wherein, when a sample not containing blood is received at the sample collection area of the first finger receiving member and caused to contact the at least one reagent at the second finger receiving member, a visible indication that the sample contains blood does not result at the second finger receiving member.

In any of the preceding or alternative embodiments, an examination device according to the present invention may be an examination glove.

In any of the preceding or alternative embodiments, the first and second finger receiving members may be continuous with and located adjacent or non-adjacent one to the other.

In any of the preceding or alternative embodiments, an examination device according to the present invention may further include a pressure rupturable encapsulation located at the second finger receiving member, and which may be generally located proximal the second closed end of the second finger receiving member.

In any of the preceding or alternative embodiments, an examination device according to the present invention may further include a sample collection element generally located at the sample collection area, and which may be integral with the first finger receiving member or may be distinct from the first finger receiving member. When the sample collection element is distinct from the first finger receiving member, it may be permanently or removably attached thereto.

In any of the preceding or alternative embodiments, an examination device according to the present invention may be fabricated from a natural or synthetic material, such as latex or polypropylene.

In any of the preceding or alternative embodiments, an examination device according to the present invention includes a developer reagent and an indicator reagent.

In any of the preceding or alternative embodiments, an examination device according to the present invention further includes a test pad at the second finger receiving member, and wherein one or both of the developer and indicator reagents may be impregnated within, absorbed into, or adsorbed onto the test pad.

In any of the preceding or alternative embodiments, the developer reagent may be selected from the group consisting of hydrogen peroxide, benzoyl peroxide, sodium peroxide, cumene hydroperoxide, magnesium peroxide, and sodium perborate.

In any of the preceding or alternative embodiments, the indicator reagent may be selected from the group consisting of gum guaiac, tetramethyl benzidine, o-toluidine, cresol, catechol, 3,3',5,5'-tetramethylbenzidine, p-toluidine, betanaphthol, pyrogallol, o-phenylenediamine, leuco malachite green, 3-amino ethylcarbazole, 4-amino antipyrine, phenol, 2,2'-azino-di-(3-ethylbenzyl)azoline sulfonic acid, and mixtures thereof.

In any of the preceding or alternative embodiments, the second finger receiving member may further include one or more compounds for enhancing a visible change in the indicator reagent, the one or more compounds being selected from the group consisting of an ester of hydroxybenzoic acid, paraben, phenol, guaiacol, p-hydroxybenzoic acid, 3,5-dimethylphenol, methyl salicylate, 3-5, dichlorophenol, p-nitrophenol, p-bromophenol, an aromatic heterocycle, a tertiary or quaternary ammonium compound having a phenyl, hydroxy alkyl or esterified hydroxy alkyl attached to the nitrogen, and quinolines or substituted derivatives thereof.

In any of the preceding or alternative embodiments, the second finger receiving member may further include one or more compounds for increasing the sensitivity and/or the specificity of a test for detecting the presence of blood performed with an examination device according to the present invention, the one or more compounds may include a peroxidase denaturing agent, urea, guanidine hydrochloride, or a metal chelating agent.

In any of the preceding or alternative embodiments, an examination device according to the present invention may be provided in a kit, wherein the examination device is packaged in a sterile environment.

In certain example (non-limiting) embodiments, there is provided by the present invention an examination device for detecting the presence of blood in a sample, including an examination glove having at least first, second, and third finger receiving members, each of the first, second, and third finger receiving members having a first open end and a second closed end and being located spaced apart from and continuous with each other of the first, second, and third finger receiving members, the first finger receiving member including a sample collection area generally located proximal the second closed end thereof for receiving a sample to be tested for the presence of blood, the second finger receiving member including a developer reagent, and the third finger receiving member including an indicator reagent, wherein, when a sample containing blood is received at the sample collection area of the first finger receiving member and caused to contact the developer and indicator reagents, a visible indication that the sample contains blood results at the third finger receiving member, and wherein, when a sample not containing blood is received at the sample collection area of the first finger receiving member and caused to contact the developer and indicator reagents, a visible indication that the sample contains blood does not result at the third finger receiving member.

In certain example (non-limiting) embodiments, there is provided by the present invention a method for detecting the presence of blood in a sample, including (a) obtaining a sample at a sample collection area located proximal a closed end of a first finger receiving member of an examination device, (b) pressing the sample to a second finger receiving member of the examination device, the second finger receiving member located spaced apart from the first finger receiving member, wherein the sample is pressed with sufficient force to cause the sample to contact at least one reagent present at the second finger receiving member, the at least one reagent present at the second finger receiving member being capable of reacting with a blood component, and (c) detecting a visible change at the second finger receiving member, wherein, when a sample containing blood is received at the sample collection area of the first finger receiving member and caused to contact the at least one reagent at the second finger receiving member, a visible indication that the sample contains blood results at the second finger receiving member, and wherein, when a sample not containing blood is received at the sample collection area of the first finger receiving member and caused to contact the at least one reagent at the second finger receiving member, a visible indication that the sample contains blood does not result at the second finger receiving member.

In any of the preceding or alternative embodiments, in a method for detecting the presence of blood in a sample according to the present invention, the second finger receiving member may include a pressure rupturable encapsulation, wherein, when the sample is pressed to the second finger receiving member, the pressure rupturable encapsulation is caused to be ruptured, thereby releasing the at least one reagent.

In any of the preceding or alternative embodiments, in a method for detecting the presence of blood in a sample according to the present invention, the method may be conducted in a one-handed operation.

In certain example (non-limiting) embodiments, there is provided by the present invention a method for detecting the presence of blood in a sample, including (a) obtaining a sample on a sample collection area located proximal a closed end of a first finger receiving member of an examination glove, (b) pressing the sample to a second finger receiving member located spaced apart from the first finger receiving member of the examination glove with sufficient force to cause the sample to contact a developer reagent or an indicator reagent present at the second finger receiving member, (c) pressing the sample to a third finger receiving member located spaced apart from the first and the second finger receiving members of the examination glove with sufficient force to cause the sample to contact a developer reagent or an indicator reagent present at the third finger receiving member, and (d) detecting a visible change at the second finger receiving member or at the third finger receiving member, wherein, each of a developer reagent and an indicator reagent is employed in at least one of steps (b) and (c), and wherein, when a sample containing blood is received at the sample collection area of the first finger receiving member and caused to contact the developer and indicator reagents, a visible indication that the sample contains blood results at one of the second finger receiving member or the third finger receiving member, and wherein, when a sample not containing blood is received at the sample collection area of the first finger receiving member and caused to contact the developer and indicator reagents, a visible indication that the sample contains blood does not result at one of the second finger receiving member or the third finger receiving member.

Certain examples of the invention are now below described with respect to certain non-limiting embodiments thereof as illustrated in the following drawings wherein:

DETAILED DESCRIPTION OF THE PREFERRED EMBODIMENTS

The present invention relates to examination devices, including examination gloves, for the detection of blood, and in particular for the detection of occult (hidden) blood. In certain embodiments, examination devices according to the present invention include an encapsulation for housing at least one reagent that will react with one or more blood components present in a sample and which will register a visible change when such a reaction occurs. In certain embodiments, when blood is present in the sample, one or more blood components react with developer and/or indicator reagent(s) to register a chromatic change which indicates that the sample contains blood.

In certain embodiments, examination devices according to the present invention are useful in fecal occult blood testing, and as such may be used, for example, for the early detection of bleeding esophageal varices, colon polyps, colon cancer, esophagitis, gastritis, gastrointestinal trauma, gastrointestinal tumors, hemorrhoids, fissures, inflammatory bowel disease, peptic ulcer, complications resulting from gastrointestinal surgery, and angiodysplasia of the colon. Examination devices according to the present invention may be used in human and animal medical testing, as well as in non-medical applications such as forensic testing.

Developer and indicator reagents which may be used in the present invention are known in the art and include conventional reagents which permit the desired reaction(s) to occur. Examination devices according to the present invention further include a member for obtaining a sample, such as a stool sample or other secretion. The presence of occult blood in the sample may be indicative, for example, of trauma or disease when an examination device according to the present invention is used diagnostically. As will be apparent to those of skill in the art, examination devices according to the present invention may be used in any application where there exists the need to determine if a particular sample is or contains blood or blood components. For example, in addition to medical uses such as proctologic and gynecologic examinations, examination devices according to the present invention are useful in other medical applications where the need exists to detect the presence of blood in a sample, and are further useful in non-medical applications.

Figure 1:
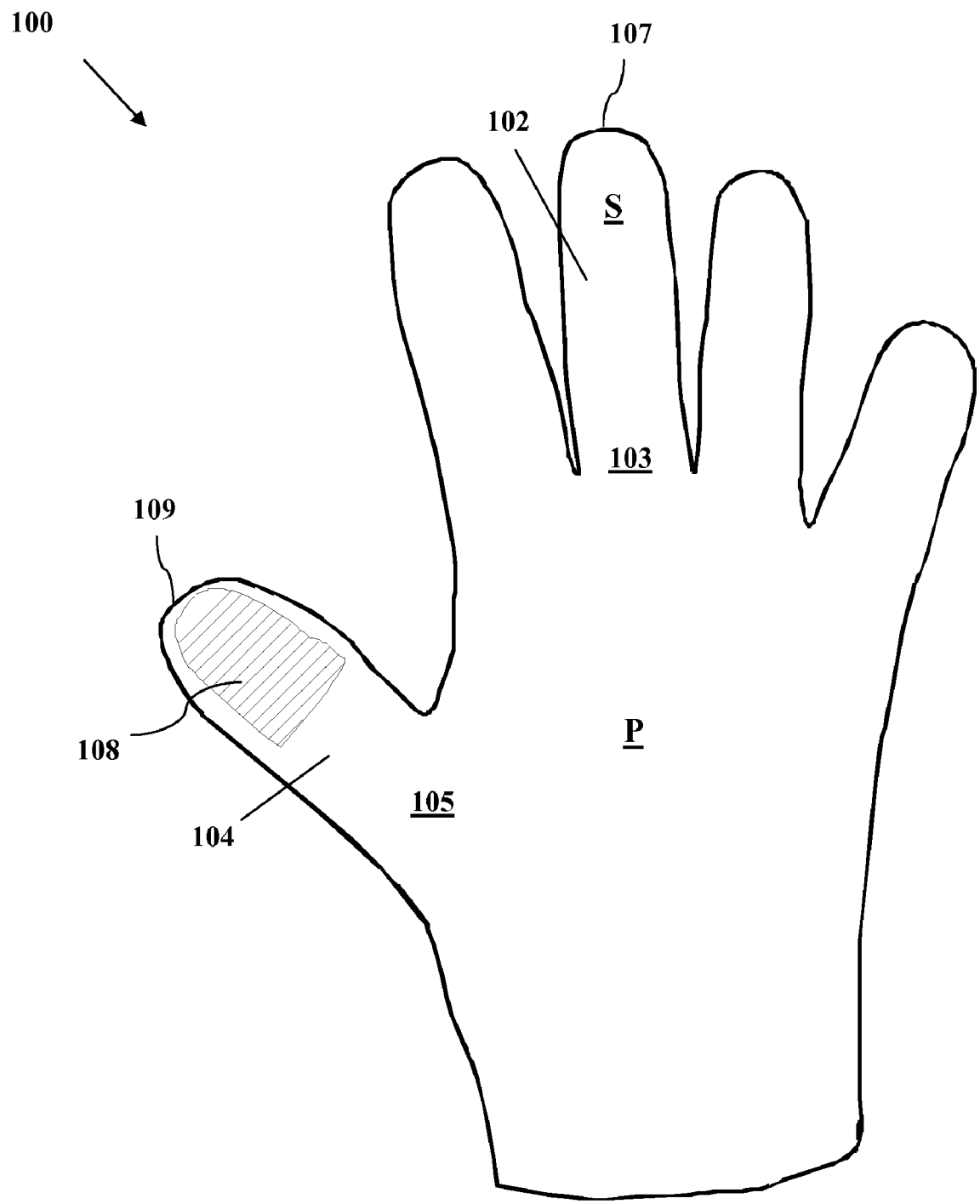
FIG. 1 shows a front view of one embodiment of an examination device according to the present invention.

Turning now to FIG. 1, one embodiment of an examination device according to the present invention is shown. In this embodiment, the examination device includes an examination glove 100 that is shown such that, once examination glove 100 is placed on a wearer's hand, the wearer's palm is oriented as indicated by P. Examination glove 100 in this embodiment includes at least a first finger receiving member 102 and a second finger receiving member 104 for placement over the wearer's middle finger and thumb, respectively.

For hygienic and safety reasons, examination glove 100 will typically include five finger receiving members such that the wearer's entire hand is covered, but embodiments having less than five finger receiving members are also contemplated by, and within the scope of, the present invention. Such embodiments may be particularly useful, for example, in non-medical applications, such as testing for blood at a crime scene where it may not be necessary to cover the wearer's entire hand. In such embodiments, the examination glove is generally more easily placed on and removed from the wearer's fingers, and is relatively less expensive to manufacture as a result of reduced material and manufacturing requirements.

Similarly, "examination device", as the term is used herein, broadly refers to devices including at least first and second finger receiving members, where one of the finger receiving members is for receiving a sample and the other includes at least one reagent that is capable of reacting with one or more blood components such that, when the sample is pressed to the finger receiving member having at least one reagent, a visible indication that the sample is or contains blood results at such finger receiving member. The first and second finger receiving members may be distinct members that are not continuous with each other and may be placed directly on the wearer's fingers or over the fingers of, for example, an existing examination glove, or they may be continuous with each other and may be located adjacent or non-adjacent to each other. As will be apparent to those of skill in the art from the instant teachings, examination devices according to the present invention include any number of configurations that permit the presence of occult blood to be detected.

Examination devices according to the present invention may be fabricated from any suitable material, and in particular may be fabricated from materials that are already approved and/or deemed acceptable for medical use. Examination devices according to the present invention may, for example, be fabricated from either natural (e.g., latex) or synthetic (e.g., plastic, such as polyvinyl chloride or polypropylene) materials depending on the intended application of the examination device, as well as on other factors (such as allergic sensitivities of the wearer). Generally, examination devices according to the present invention conform tightly to the wearer's hand to permit sufficient tactile sensitivity, such that a clinician may properly conduct a proctologic examination in addition to obtaining and testing a patient's stool sample if used for such purpose.

Similarly, examination devices according to the present invention may be fabricated in any suitable conventional manner. For example, medical examination gloves are typically fabricated with a powder coating, but they may also be fabricated without a powder coating, or may be provided with an alternative coating (see, for example, in this regard, U.S. Pat. Nos. 6,016,570 and 4,143,109, hereby incorporated by reference in their entirety). Examination devices according to the present invention may also be made of several layers, for example they may comprise an outer layer of elastomeric material and an inner layer of elastomeric material (e.g., carboxylated styrene butadiene latex bonded to the outer layer), and may include lubricating corn starch particles embedded in the inner layer.

Figure 4:
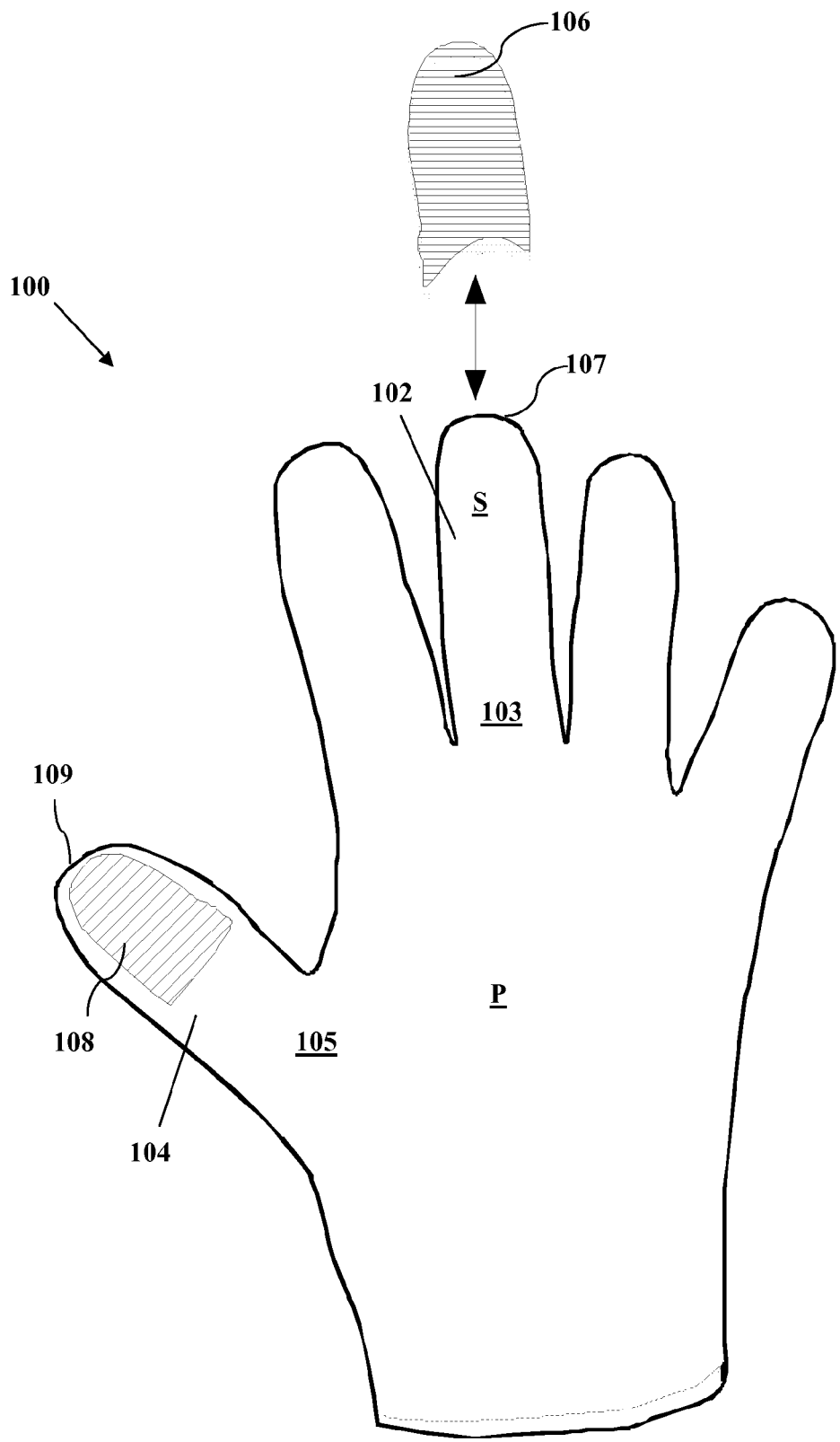
FIG. 4 shows a front view of one embodiment of an examination device according to the present invention including a removable sample collection element.

With reference again to the embodiment illustrated in FIG. 1, each of first and second finger receiving members 102, 104 has a first open end 103 and 105 (open with respect to the interior of examination glove 100), respectively, and a second closed end, 107 and 109, respectively, at the tip portion thereof. A sample collection area indicated at S is located generally proximal second closed end 107 of first finger receiving member 102, and a sample collection element 106 may be present at sample collection area S, as illustrated in FIG. 4 and as described in greater detail below.

In the embodiment illustrated in FIG. 1, examination glove 100 may optionally include a test pad 108 for providing a matrix upon which the reaction(s) may occur. One or more test reagent(s) may, in certain embodiments, be impregnated into, absorbed within, or adsorbed onto test pad 108. As such, in this embodiment, the reaction(s) necessary to visually detect the presence of blood in a sample may therefore occur at the second finger receiving member 104 simply by pressing the sample (located in this embodiment at sample collection area S of first finger receiving member 102) to the tip area of the wearer's thumb over which second finger receiving member 104 having the test reagent(s) is located. When, in certain embodiments described below, at least one test reagent is encapsulated at second finger receiving member 104, the sample may be pressed with sufficient force to cause the encapsulation to rupture and release the test reagent(s).

Developer and indicator reagents suitable for use in the present invention include, for example, all conventional reagents that permit the detection of blood in a sample. For example, peroxide compounds, such as hydrogen peroxide, are typically used as developer reagents, and gum guaiac is typically used as an indicator reagent. Other art-recognized peroxide compounds suitable for use in the present invention include, for example and without limitation, benzoyl peroxide, sodium peroxide, cumene hydroperoxide, magnesium peroxide and sodium perborate. If blood is present in a sample, heme molecules present in the blood will catalyze the release of oxygen from the peroxide compound. The released oxygen then changes the color of the gum guaiac from colorless to blue, providing a visible indication that blood is present in the sample. In certain embodiments according to the present invention, a hydrogen peroxide developer reagent is provided in liquid form, whereas for certain applications it may be provided in solid form.

Any indicator compound that registers a visible change in the presence of oxygen may be used in the present invention. For example, gum guaiac is conventionally used as an indicator in occult blood testing, and is suitable for use in the present invention. In a preferred embodiment, gum guaiac is solubilized with a suitable solvent (for example and without limitation methanol, ethanol, or propanol) for encapsulation or impregnation on test pad 108, which may be of any suitable material, including conventional materials such as filter paper or any porous paper that permits the desired reactions to occur. Other indicator reagents suitable for use in the present invention include, for example, chromogen, such as leuco dyes including tetramethyl benzidine and o-toluidine, cresol, catechol, 3,3',5,5'-tetramethylbenzidine, p-toluidine, betanaphthol, pyrogallol, o-phenylenediamine, leuco malachite green, 3-amino ethylcarbazole, 4-amino antipyrine, phenol, 2,2'-azino-di-(3-ethylbenzyl)azoline sulfonic acid, and mixtures thereof. When such dyes are used, test pad 108 may further be coated to prevent oxidation of the chromogen. Moreover when the indicator is impregnated into test pad 108, various factors, such as the material of test pad 108, and the solubility of the chosen indicator, will determine the amount of indicator needed for effectiveness.

Moreover, various enhancing agents may be added to intensify the color change, thereby making it easier for the wearer to recognize. Suitable enhancers for use in the present invention include, for example, phenolic compounds, such as esters of hydroxybenzoic acid, parabens, phenol, guaiacol, p-hydroxybenzoic acid, 3,5-dimethylphenol, methyl salicylate, 3-5, dichlorophenol, p-nitrophenol, and p-bromophenol; as well as monocyclic nitrogen-containing aromatic heterocyclic compounds; tertiary or quaternary ammonium compounds having a phenyl, hydroxy alkyl or esterified hydroxy alkyl attached to the nitrogen; or quinoline or a substituted derivative thereof.

Further, various agents may be added to the developer and/or indicator reagents to increase the sensitivity and/or specificity of the blood detection test being carried out with examination devices according to the present invention. For example, it is known that stool samples may include certain plant peroxidases which can result in false positive test results. As such, a peroxidase denaturing agent (e.g., urea or guanidine hydrochloride) may be provided in combination with a metal chelating agent to sequester calcium and magnesium ions required for peroxidase activity. Still further, when a leuco dye is used as the indicator reagent, polar solvents (e.g., dimethyl sulfoxide and dimethyl formamide) may be employed to stabilize the peroxide reagent and the dye.

In certain embodiments, the developer and indicator reagents are provided together at the same finger receiving member, in any suitable manner, such as those discussed herein. Such a configuration offers numerous benefits with respect to the manufacture and use of the inventive examination devices. For example, patients with arthritic conditions are able to use examination devices according to the present invention without the need for excessive bending of the fingers. Moreover, such configurations are relatively easy to manufacture by incorporating the reagent(s) directly into or onto the examination device, and are further readily adaptable to use with existing devices, such as examination gloves, as a result of having relatively fewer components. It is further contemplated that other reagent(s) that permit the detection of occult blood in a sample may be used in examination devices according to the present invention, including individual reagents which may alone react with one or more blood components to register a visible or other change when blood is present in a sample.

As will be apparent to those of skill in the art, it may further be desirable in certain embodiments to include other compounds in combination with developer and/or indicator reagent(s). For example, it is known that heme molecules in the blood react readily with hydrogen peroxide in an acid environment, and as such a developer reagent may include an acid, or an acid may be impregnated into test pad 108 such that it catalyzes the reaction between the heme molecules and hydrogen peroxide when a developer encapsulation ruptures in such embodiments where an encapsulation is used. Of course, the choice of such an acid will depend on the particular conditions associated with the examination device. For example, a weakly dissociated acid may be desired where it will contact test pad 108, so as not to degrade it. When test pad 108 is made of particular materials, such as filter paper, an organic acid may be desirable (for example, acetic or citric acid).

Generally speaking, developer and indicator reagents, as well as other reagents including those described above, may be provided in the present invention any manner that permits them to carry out the desired reaction(s). For example, they may be provided together in various forms of encapsulation, or they may be impregnated into, absorbed within, or affixed to test pad 108. Encapsulations may, in certain embodiments, be affixed to test pad 108 or may be integrated with test pad 108 in a suitable manner (such as where the test pad forms the base of the encapsulation).

Encapsulations suitable for use in the present invention refer generally to all art-recognized forms of encapsulation that permit all test reagent(s) to be associated, in certain embodiments, with the same finger receiving member while permitting the desired reaction(s) to occur. Furthermore, in embodiments employing encapsulation, the reagent(s) being encapsulated should generally not come into contact with the ambient atmosphere until released from the encapsulation. For example, in certain embodiments, suitable encapsulations permit a developer to rupture from its encapsulation when pressure is applied by the sample-containing finger, such that the developer will react with heme molecules present in any blood. Thereafter in such embodiments, oxygen thereby released may react with an indicator reagent, which may also be encapsulated, either alone or with the developer, or which may be provided at a test pad.

If the indicator is encapsulated, it should be encapsulated so that it is capable of reacting in the desired manner. It is expected in certain embodiments that the developer, sample, and indicator may mix at substantially the same time and achieve the desired test result, however if it is determined that for any particular application it is desirable to contact the developer with the sample prior to contact with the indicator, the indicator may, for example, be encapsulated such that a greater pressure is required to rupture its membranous coating than is required to rupture the membranous coating of the developer reagent (for example, through the use of a thicker membrane, multiple membranes, or through the use of a higher viscosity solution that creates greater internal pressure on the membrane).

Likewise, if, in certain embodiments, an indicator is impregnated into test pad 108, a developer may be encapsulated in such a way as to permit the desired reaction, which includes both the developer, sample and indicator mixing concurrently, as well as the developer and sample mixing prior to mixing with the indicator. The determination of how such reactions should occur, and consequently the configuration of such encapsulation, impregnation or other means of providing the reagents, will generally depend on the particular reagents in use (including the specific active compounds) as well as other compounds that may be present.

Encapsulation technologies suitable for use in the present invention include, for example, the use of various polymeric and other materials that are capable of being ruptured in a desired manner under sufficient pressure and/or when exposed to sufficient sheer stress to permit the blood detection test to be carried out, but that otherwise safely and reliably maintain their integrity.

Further, encapsulations useful in accordance with the present invention may be fabricated directly into the examination device, or may be affixed to the device, including being provided separately from the examination device such that they may be retrofitted onto a pre-fabricated examination devices, such as an examination glove, by a wearer prior to use, thus, again, providing a great deal of flexibility in the manner in which examination devices according to the present invention are provided to the wearer. This flexibility further permits the use of examination devices according to the present invention in the greatest number of applications, and in such a way as to permit flexibility with their manufacture.

Once the specific configuration and composition of the encapsulation(s) and reagent(s) has been determined, known methods may be employed for their manufacture, for example coating a thin film over a desired solution to form a pressure-sensitive capsule.

Figure 2:
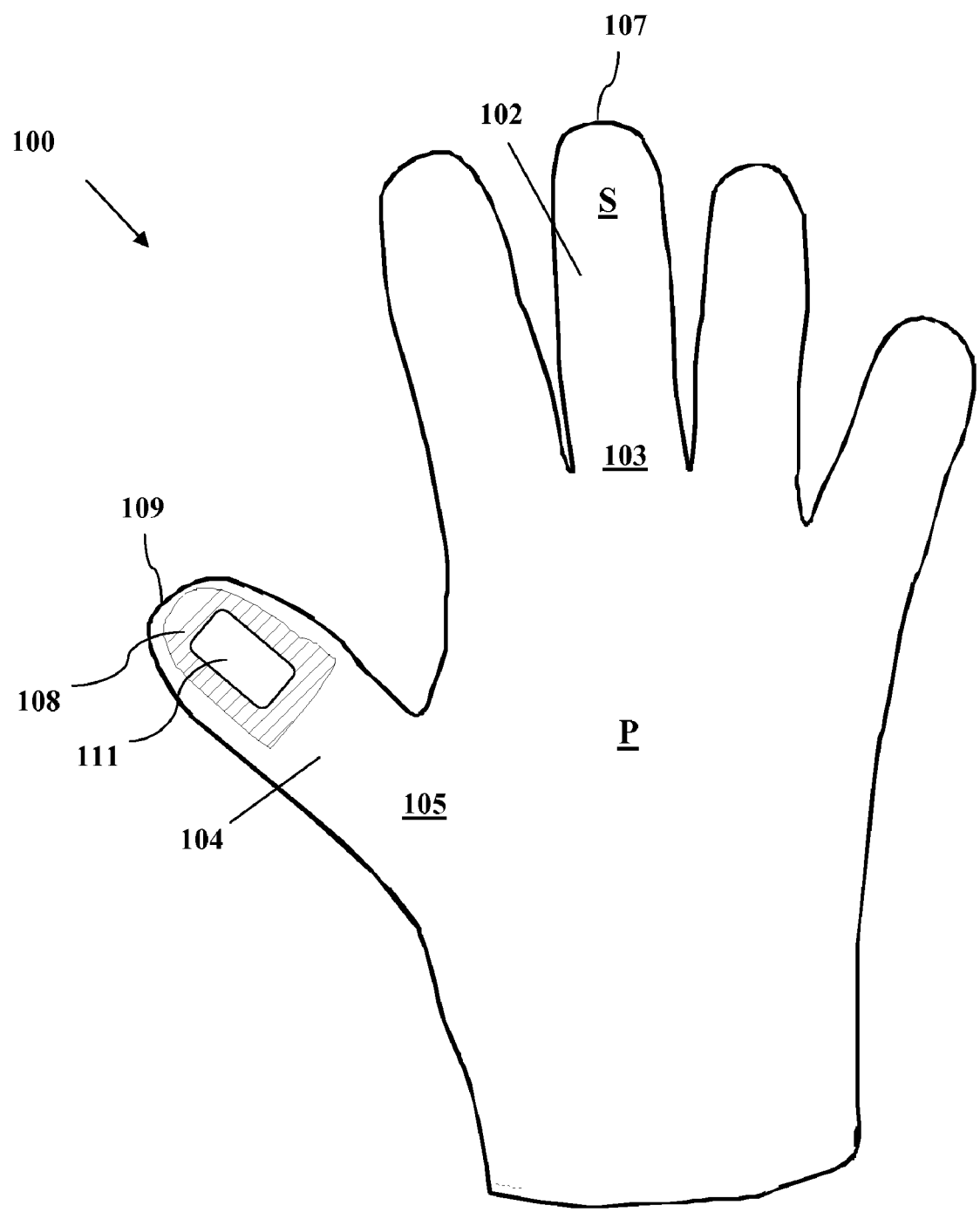
FIG. 2 shows a front view of one embodiment of an examination device according to the present invention including a developer/indicator encapsulation.
Figure 3A:
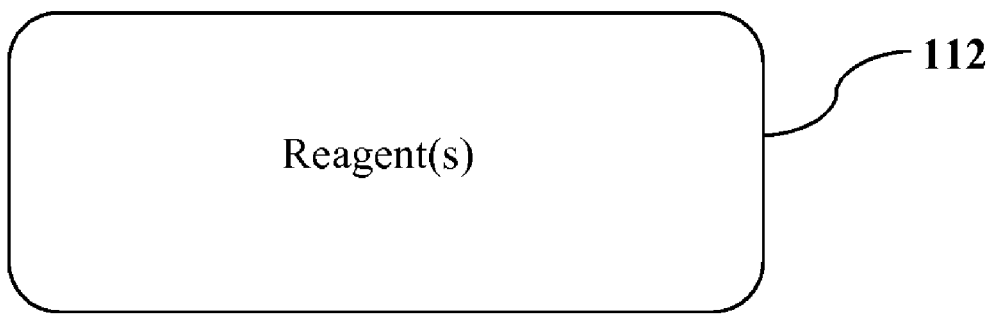
FIGS. 3A-3C illustrate various embodiments of reagent encapsulations useful in examination devices according to the present invention.
Figure 3B:
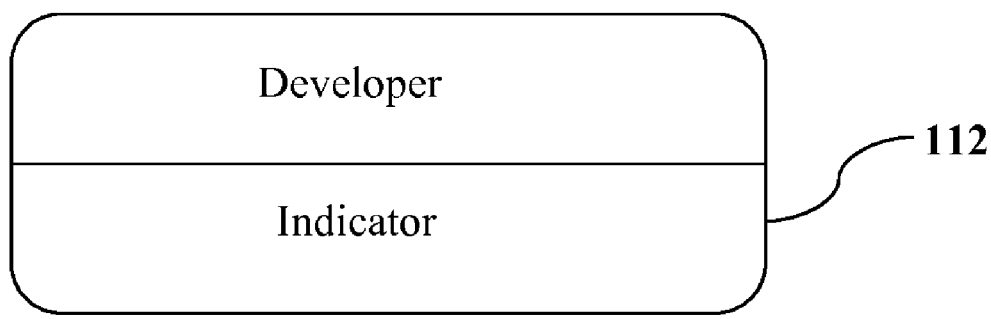
Figure 3C:
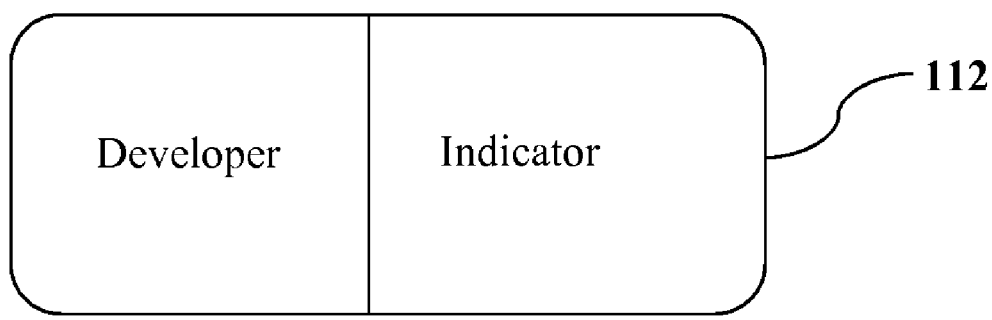

As illustrated in the embodiment shown in FIG. 2, the reagent(s) may be encapsulated in a somewhat larger rupturable encapsulation 111, so long as encapsulation 111 ruptures in a controlled manner that permits the blood detection test to take place. Encapsulation 111 may be configured to retain one or more reagents in a single housing, such as shown in FIG. 3A and may be configured to house at least two reagents, for example developer and indicator reagents, separately, such as shown, for example, in FIGS. 3B and 3C. Any configuration that permits the desired reaction(s) to take place is suitable for use in accordance with the present invention.

The particular materials from which encapsulation 111 may be fabricated include various polymeric and other materials that permit the desired reaction(s) to occur, either such that both reagents mix concurrently with the sample when there is more than one reagent, or such that the developer reagent mixes with the sample prior to release of the indicator reagent. Further, encapsulation 111 may be provided alone or in combination with test pad 108 for retrofitting onto an existing examination glove.

Turning to the embodiment illustrated in FIG. 4, an examination glove 100 having a sample collection element 106 is shown. Sample collection element 106 is, in this embodiment, provided at sample collection area S of first finger receiving member 102 and is permanently or removably attached thereto, depending on the desired configuration of examination glove 100 for various applications.

For example, in certain applications it may be desirable to supply sample collection element 106 as a standalone removable sheath which may be fitted over the tip of first finger receiving member 102 of a pre-fabricated examination glove, whereas in other applications it may be desirable to manufacture sample collection element 106 into first finger receiving member 102, either as a distinct non-removable member or as an integral part of first finger receiving member 102. It is understood that the "tip" of the finger as used herein is defined broadly to include any portion of the finger that is located generally above the wearer's knuckle and proximal second closed end 107 of first finger receiving member 102, and also includes the entire circumference of the wearer's finger upon which first finger receiving member 102 is placed.

Sample collection element 106 may be made of any suitable material, the choice of which will generally depend on the particular application for which it will be used. For example, it may be a low-friction material suitable for insertion into a body cavity (such as the rectum). Suitable plastic, elastomeric and other materials for such purposes are well-known in the art. Likewise, sample collection element 106 may be impregnated with a lubricant, or a lubricant may be provided to its outer surface in any form that permits its use during clinical or at-home testing, so as to increase patient comfort.

Further, sample collection element 106 may be configured so as to otherwise facilitate the collection of a biological sample from a body cavity, such as by the incorporation of grooves, ridges, dimples and so forth to assist and facilitate the collection of the sample upon withdrawal of sample collection element 106 from the body cavity.

The configuration of, and choice of material for, sample collection element 106 will depend on its intended application. For example, when used in medical examinations, it should generally be made of a material that is substantially inert to sensitive body cavity linings, and should be configured such that it is suitable for use within the body. On the other hand, sample collection element 106 may be made of a different material and/or may be otherwise configured (thus allowing for potential material and/or manufacturing savings) where such considerations are not present, for example in certain non-medical applications.

Likewise, as certain patients may have allergic sensitivities to conventional materials that are used in medical applications (such as latex), sample collection element 106 may be fabricated from particular materials to suit the needs of these patient populations. In this regard, in certain embodiments, the individual components of an examination device according to the present invention may be provided separately so that a clinician may configure the examination device to suit a patient's particular needs. For example, where a patient has a particular sensitivity to a material from which sample collection element 106 may typically be fabricated, the clinician may instead select an alternative sample collection element that is made from another material that is uniquely suited to that patients' needs, which may then be placed over the finger of a pre-fabricated examination device, such as an examination glove, having the test reagent(s), or over the finger of a pre-fabricated examination device to which the test reagent(s) are then added, for example by then affixing to the thumb of an examination glove an encapsulation including the test reagent(s). As will be readily apparent to those of skill in the art from the instant teachings, examination devices according to the present invention may be configured and fabricated in any number of suitable ways to meet the needs of both clinicians and patients for medical applications and the needs of the wearer for non-medical applications, while permitting their herein described diagnostic and other uses.

Figure 5:
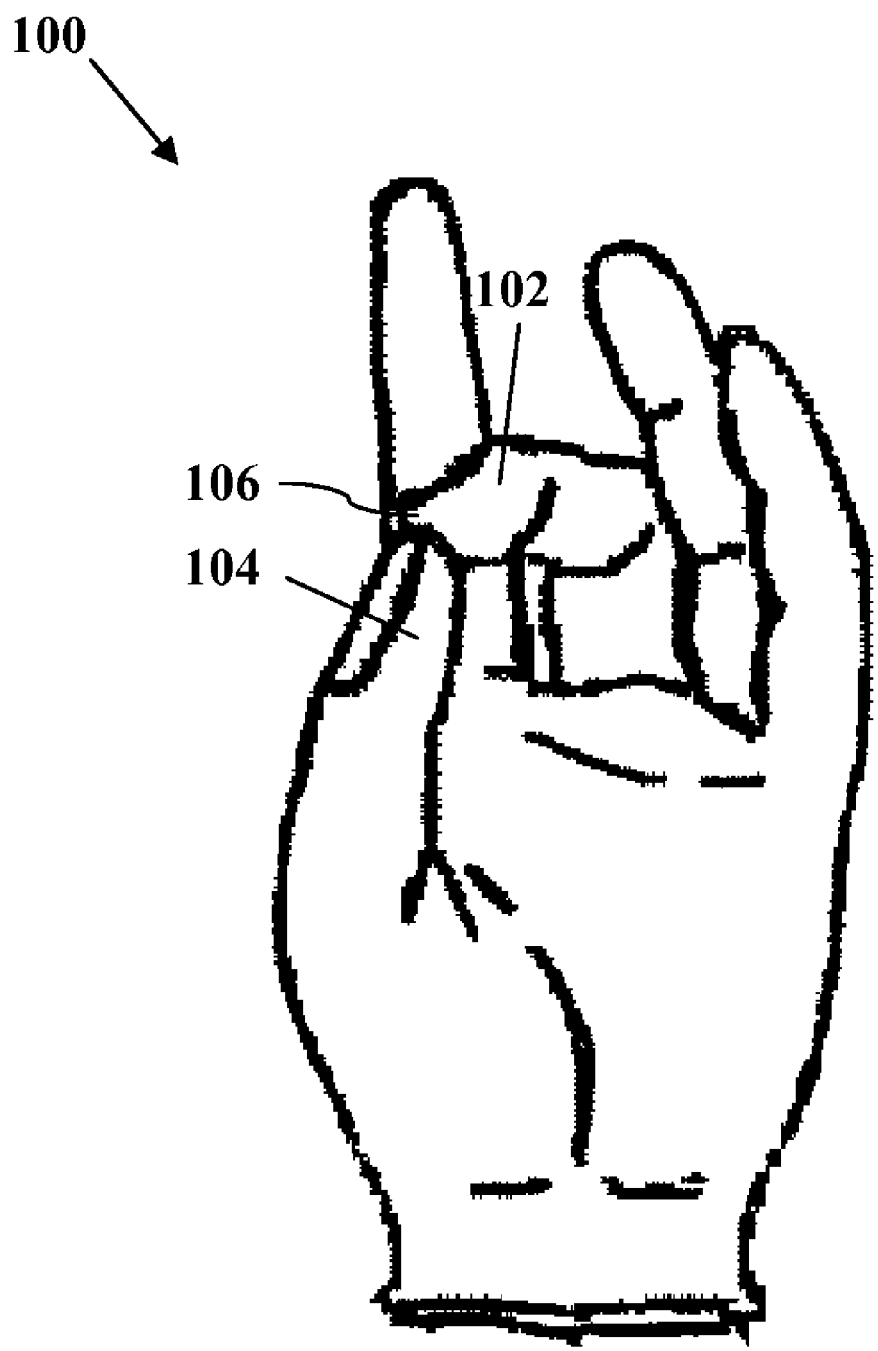
FIG. 5 illustrates the use of one embodiment of an examination device according to the present invention.

Turning now to FIG. 5, the use of one embodiment of an examination glove 100 according to the present invention is illustrated. As shown in FIG. 5, sample collection element 106 on first finger receiving member 102 is used to obtain a sample from a patient at the tip thereof. Thereafter, the tip of first finger receiving member 102 is pressed, as illustrated, to the tip of second finger receiving member 104, which includes an encapsulation including one or more reagents, and which may include other compounds, as discussed above. When sufficient pressure is applied by the wearer at the tip of first finger receiving member 102, the encapsulation ruptures, releasing the reagent(s) such that the reagent(s) come into contact with the sample. As discussed, if the sample contains blood and/or blood components, there will be a change (such as a color change) that will be visible at second finger receiving member 104.

Figure 6:
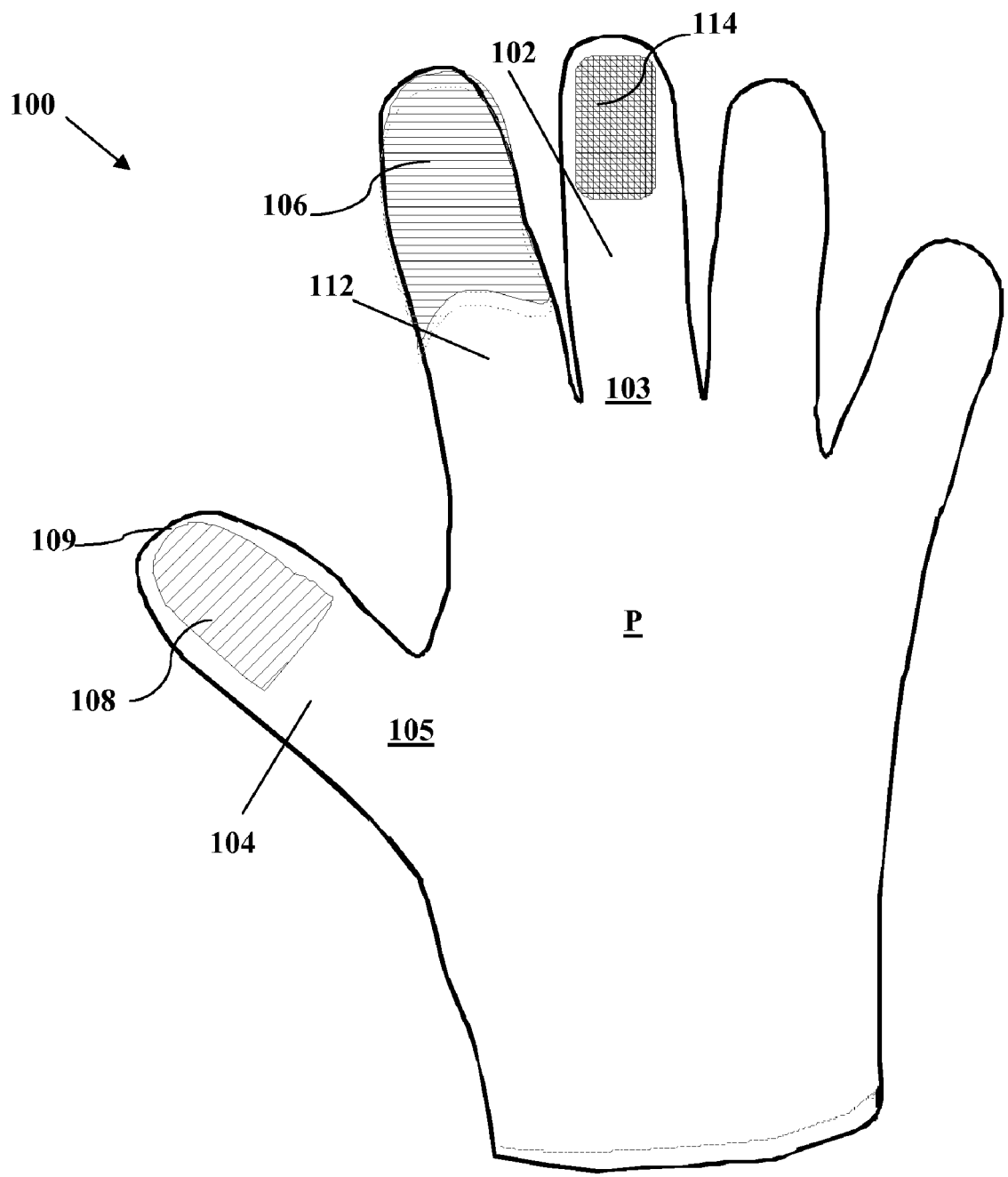
FIG. 6 shows another embodiment of an examination device according to the present invention.
Figure 7:
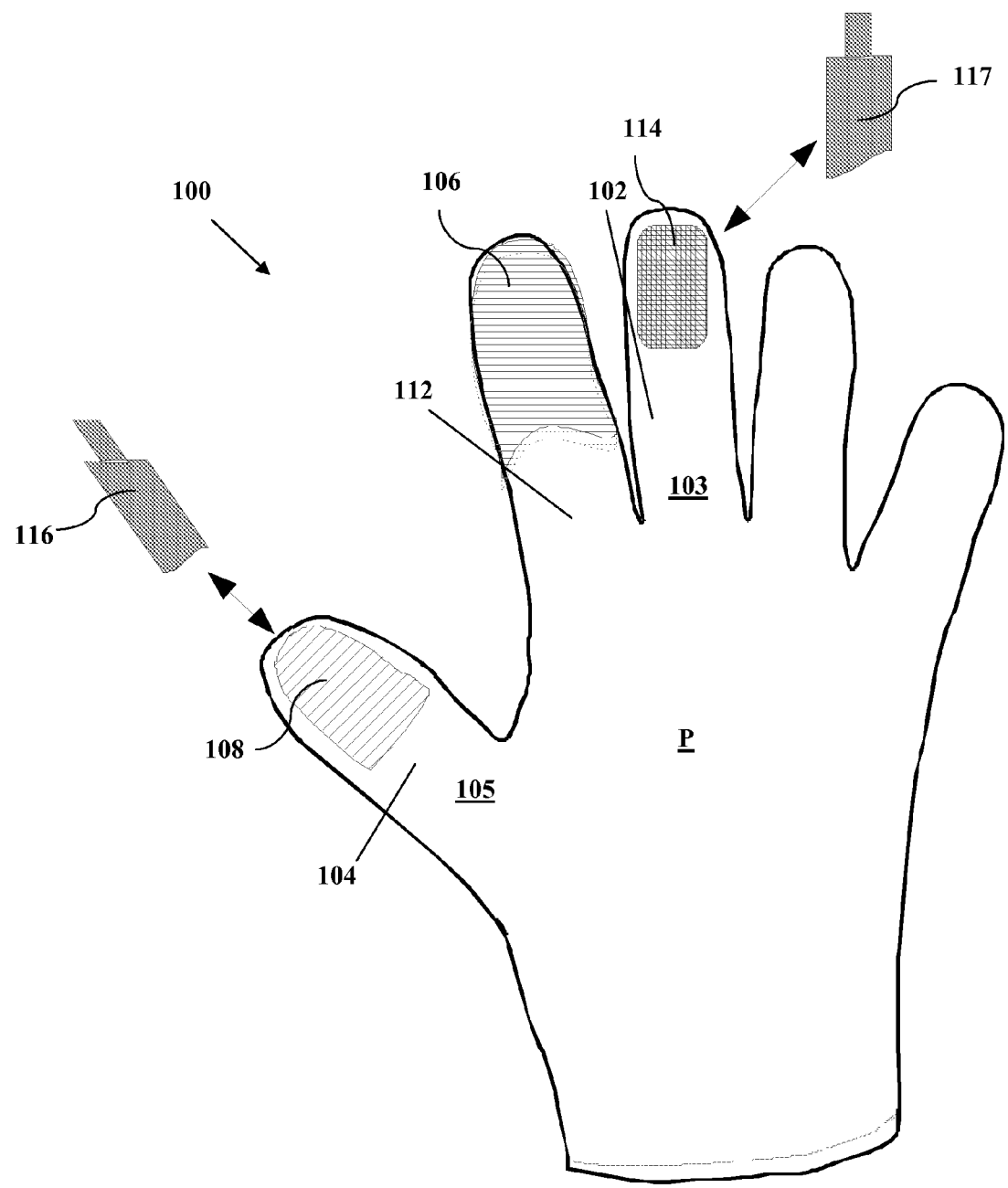
FIG. 7 shows another embodiment of an examination device according to the present invention including removable pull-tabs over each of the developer reagent and support member impregnated with indicator reagent.

Illustrated in FIGS. 6 and 7 are alternate embodiments of examination devices according to the present invention, in which three finger receiving members, 102, 104 and 112 are employed to carry out the blood detection test. In these embodiments, for example, sample collection element 106 is present on third finger receiving member 112; the indicator reagent is associated with test pad 108 on second finger receiving means 104, such as by impregnation into test pad 108 or in an encapsulation affixed to test pad 108 (not shown); and the developer reagent is provided in an encapsulation 114 on first finger receiving means 102.

In this embodiment, the test is then performed by obtaining a sample with sample collection element 106, pressing the tip of third finger receiving member 112 having the sample to the tip of second finger receiving member 104, so as to cause the sample to smear onto test pad 108 (which, in this embodiment, includes an indicator reagent); and then pressing the tip of first finger receiving member 102 to the tip of second finger receiving member 104 to cause to mix the developer reagent in encapsulation 114 with the sample and indicator reagent on test pad 108, thus permitting the test reaction to occur. Alternatively, the indicator and developer reagents may be placed on alternate fingers, and/or the test may be carried out such that the developer is first contacted to the sample.

In certain embodiments, the developer and indicator reagents should not mix with the ambient environment prior to use and/or need to be secured to the examination device to prevent their separation from the examination device, they may be enclosed in any suitable manner, such as those discussed herein, or they may, as illustrated in the embodiment shown in FIG. 7, be covered with one or more removable tabs 116, 117 that are removed just prior to use, thus exposing the reagents.

Once given the above disclosure, many other features, modifications, and improvements will become apparent to the skilled artisan. Such features, modifications, and improvements are therefore considered to be part of this invention, without limitation imposed by the example embodiments described herein. Moreover, any word, term, phrase, feature, example, embodiment, or part or combination thereof, as used to describe or exemplify embodiments herein, unless unequivocally set forth as expressly uniquely defined or otherwise unequivocally set forth as limiting, is not intended to impart a narrowing scope to the invention in contravention of the ordinary meaning of the claim terms by which the scope of the patent property rights shall otherwise be determined. All references discussed and disclosed herein are hereby incorporated by reference in their entirety.

What is claimed is:

1. An examination device for detecting the presence of blood in a sample, comprising:
    an examination glove having at least first, second, and third finger receiving members, each of said first, second, and third finger receiving members having a first open end and a second closed end and being spaced apart from and continuous with each other of said first, second, and third finger receiving members,
    said first finger receiving member including a sample collection area disposed upon said first finger receiving member and generally located proximal said second closed end of said first finger receiving member for receiving a sample to be tested for the presence of blood,
    said second finger receiving member including at least one reagent region including a developer reagent capable of reacting with a blood component disposed upon said second finger receiving member and generally located proximal to said second closed end of said second finger receiving member, and
    said third finger receiving member including at least one reagent region including an indicator reagent disposed upon said third finger receiving member and generally located proximal to said second closed end of said third finger receiving member,
    wherein, when a sample containing blood is received at said sample collection area of said first finger receiving member and caused to contact said developer reagent disposed upon said second finger receiving member and said indicator reagent disposed upon said third finger receiving member, a visible indication that said sample contains blood results at said second closed end of said third finger receiving member, and when a sample not containing blood is received at said sample collection area of said first finger receiving member and caused to contact said developer reagent disposed upon said second finger receiving member and said indicator reagent disposed upon said third finger receiving member, a visible indication that said sample contains blood result does not result at said second closed end of said third finger receiving member.

2. An examination device for detecting the presence of blood in a sample according to claim 1, wherein said examination device is an examination glove.

3. An examination device for detecting the presence of blood in a sample according to claim 1, wherein said first and second finger receiving members are continuous with and located adjacent or non-adjacent one to the other.

4. An examination device for detecting the presence of blood in a sample according to claim 1, further comprising a sample collection element generally located at said sample collection area, wherein said sample collection element is integral with said first finger receiving member or is distinct from said first finger receiving member.

5. An examination device for detecting the presence of blood in a sample according to claim 4, wherein, when said sample collection element is distinct from said first finger receiving member, said sample collection element is permanently or removably attached to said first finger receiving member.

6. An examination device for detecting the presence of blood in a sample according to claim 1, wherein said examination device is fabricated from a natural or synthetic material.

7. An examination device for detecting the presence of blood in a sample according to claim 6, wherein said examination device is fabricated from latex or polypropylene.

8. An examination device for detecting the presence of blood in a sample according to claim 1, wherein said second finger receiving member further includes a test pad.

9. An examination device for detecting the presence of blood in a sample according to claim 1, wherein said developer reagent is selected from the group consisting of hydrogen peroxide, benzoyl peroxide, sodium peroxide, cumene hydroperoxide, magnesium peroxide, and sodium perborate.

10. An examination device for detecting the presence of blood in a sample according to claim 1, wherein said indicator reagent is selected from the group consisting of gum guaiac, tetramethyl benzidine, o-toluidine, cresol, catechol, 3,3',5,5'-tetramethylbenzidine, p-toluidine, betanaphthol, pyrogallol, o-phenylenediamine, leuco malachite green, 3-amino ethylcarbazole, 4-amino antipyrine, phenol, 2,2'-azino-di-(3-ethylbenzybazoline sulfonic acid, and mixtures thereof.

11. An examination device for detecting the presence of blood in a sample according to claim 1, wherein said third finger receiving member further includes one or more compounds for enhancing a visible change in said indicator reagent, said one or more compounds being selected from the group consisting of an ester of hydroxybenzoic acid, paraben, phenol, guaiacol, p-hydroxybenzoic acid, 3,5-dimethylphenol, methyl salicylate, 3-5, dichlorophenol, p-nitrophenol, p-bromophenol, an aromatic heterocycle, a tertiary or quaternary ammonium compound having a phenyl, hydroxy alkyl or esterified hydroxy alkyl attached to the nitrogen, and quinolines or substituted derivatives thereof.

12. An examination device for detecting the presence of blood in a sample according to claim 1, wherein said second or third finger receiving member further includes one or more compounds for increasing the sensitivity and/or the specificity of a test for detecting the presence of blood performed with said examination device, said one or more compounds being selected from the group consisting of a peroxidase denaturing agent, urea, guanidine hydrochloride, and a metal chelating agent.

13. An examination device for detecting the presence of blood in a sample according to claim 1, wherein said developer reagent is in liquid form.

14. A method for detecting the presence of blood in a sample, comprising:
    (a) obtaining a sample suspected of containing blood at a sample collection area disposed upon and generally located proximal to a closed end of a first finger receiving member of an examination device,
    (b) pressing said sample to a reagent region including a developer reagent capable of reacting with a blood component disposed upon and generally located proximal to a closed end of a second finger receiving member of said examination device spaced apart from said first finger receiving member of said examination device;
    (c) pressing said sample to a reagent region including an indicator reagent disposed upon and generally located proximal to a closed end of a third finger receiving member of said examination device, such that, if a blood component is present in said sample, said blood component reacts with said developer reagent and said indicator reagent to cause a visible change in said indicator reagent; and
    (d) observing if a visible change occurs in said sample.

* * * * *